United States Patent
Bodenschatz et al.

[19]

[11] Patent Number: 6,063,048

[45] Date of Patent: May 16, 2000

[54] ELASTIC JOINT SUPPORT

[75] Inventors: Stefan G. A. Bodenschatz, Buxtehude, Germany; Sherry A. Hinds, Goshen, Ohio; Thorsten Stradt, Hamburg, Germany; Richard G. Taylor, Cincinnati, Ohio; John R. Truitt, Cincinnati, Ohio; S. Michael Wiesemann, Cincinnati, Ohio

[73] Assignee: Futuro, Inc., Wilton, Conn.

[21] Appl. No.: 08/728,888

[22] Filed: Oct. 10, 1996

[51] Int. Cl.⁷ ............................................. A61F 13/00
[52] U.S. Cl. .................. 602/62; 602/20; 602/23; 602/26; 602/63; 2/22; 2/24
[58] Field of Search .................. 602/3, 20, 23, 602/26, 60–65, 74, 75; 2/455, 456, 16, 24, 62, 22

[56] References Cited

U.S. PATENT DOCUMENTS

| D. 259,058 | 4/1981 | Marshall | D24/64 |
|---|---|---|---|
| D. 273,331 | 4/1984 | Gruber | D24/64 |
| D. 331,801 | 12/1992 | Schiono | D24/190 |
| 663,749 | 12/1900 | Gorse . | |
| 3,703,171 | 11/1972 | Schlavitto . | |
| 3,804,084 | 4/1974 | Lehman . | |
| 3,934,583 | 1/1976 | Hollingshead et al. . | |
| 3,945,046 | 3/1976 | Stromgren | 2/22 |
| 4,476,857 | 10/1984 | Levine | 602/20 |
| 4,492,227 | 1/1985 | Senn et al. . | |
| 4,632,106 | 12/1986 | Gramm . | |
| 5,016,621 | 5/1991 | Bender . | |
| 5,077,837 | 1/1992 | Meistrell | 2/16 |
| 5,139,477 | 8/1992 | Peters | 602/26 |
| 5,399,153 | 3/1995 | Caprio, Jr. | 602/63 |

FOREIGN PATENT DOCUMENTS 0375809  7/1990  European Pat. Off. .

*Primary Examiner*—Richard J. Apley
*Assistant Examiner*—Kim M. Lee

[57] ABSTRACT

A support brace for knee or elbow is provided that includes a sleeve of elastic material that is unidirectionally elastic in a transverse direction across the width of the brace to provide compressive support to the joint on which the brace is worn. The sleeve includes a front portion across which is disposed one or more slightly spiral shaped, or "S" shaped, support straps. The support straps are unidirectionally elastic in a longitudinal direction along their lengths to provide lift support to the joint on which the brace is worn.

14 Claims, 3 Drawing Sheets

ELASTIC JOINT SUPPORT

TECHNICAL FIELD

The present invention relates generally to support braces, and, more particularly, to an elastic brace particularly adapted for use on an individual's knee or elbow joint that provides compression, lift and support to the joint.

BACKGROUND OF THE INVENTION

Tubular or sleeve-like braces are very well known in the prior art. Elastic braces have been used for many years as knee braces or elbow supports. Such braces provide some degree of support to the joint of the person who wears the brace while that person is engaged in an activity that requires or results in significant or repeated flexing of the joint. For example, support braces of this type are frequently used to provide support to individuals having injured or degenerating knee or elbow joints. Additionally, support braces may be effectively worn on a healthy joint to stabilize, guide, and warm it during vigorous activity. Ideally, such braces are constructed and arranged so as to provide satisfactory support to the joint and surrounding ligament system while providing the highest possible wearing comfort. During the last several years, many different configurations of braces have been developed and utilized in an attempt to provide adequate knee or elbow support.

Notwithstanding recent developments and advancements in support brace design, further improvements in design are desired. For example, designers of prior art support braces have not been able to develop a brace that provides satisfactory support while including only a minimal number of requisite components. Instead, it is common in the prior art to require numerous bulky or intersecting components in order to achieve the desired support. One example of a brace of this type is disclosed in U.S. Pat. No. 4,492,227, Senn et al. issued, Jan. 8, 1995, which describes an elastic knee brace comprising an elastic tube which fits around the knee. This tube includes three distinct elastic sections (a top, a middle and a bottom), each of which provides different support and compression characteristics to the knee. The brace includes stabilizing strips which run diagonally from the top of the brace and run underneath the kneecap. The stabilizing strips are made from a bi-directionally elastic material and their purpose is to provide rotational stabilization to the knee.

Additionally, U.S. Pat. No. 3,934,583, Hollingshead et al., issued Jan. 27, 1976, describes an elastic support which may be used for either knees or elbows. The support contains an elastic foam sleeve which fits around the joint. The support includes two strips of nylon-backed foam material which extend diagonally across the support. The two strips cross just below the kneecap. Because these strips have less elasticity than the rest of the support, as a result of their nylon backing, they provide resistance to flexing of the knee. Similarly, U.S. Pat. No. 3,945,046, Stromgren, issued Mar. 23, 1976, describes an elastic knee support which is held in place by multiple elastic straps crossing diagonally over the support (going both over and under the kneecap). These straps are provided to add both lift and support to the kneecap when they are in position. Further, U.S. Pat. No. 3,703,171, Schlavitto, issued Nov. 21, 1972, describes an elastic knee brace which includes rigid planar stays located on each side of the kneecap, as well as two straps which run diagonally from the top to the bottom of the brace crossing just below the kneecap. The straps are not flexible since they are made from leather or a leather-like material. The purpose of these straps is to both support and protect the kneecap.

Thus, it is clear that a need exists for an improved brace for supporting a knee or an elbow joint. Such a support brace should be capable of providing adequate compression and support while efficiently comprising only a minimal number of parts to achieve the desired support in a more comfortable fashion. Additionally, such a support brace would be able to be manufactured from fewer parts in an economically more efficient and more productive manner.

It is therefore a primary object of the present invention to overcome the above described limitations and disadvantages in the support brace prior art.

It is another object of the present invention to provide a support brace capable of providing adequate compression and support while efficiently comprising only a minimal number of parts to achieve the desired support in a more comfortable fashion.

It is still another object of the invention to provide a support brace capable of being manufactured from fewer parts in an economically more efficient and more productive manner.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as described herein, an improved support brace for a knee or elbow is provided. The support brace generally includes a sleeve of substantially tubular elastic material that is elastic in a traverse direction across the limb as worn. This unidirectional elastic sleeve advantageously provides compression to the protected joint. Additionally, the brace includes a support strap of material that is elastic in a longitudinal direction along its length. The support strap is disposed in a diagonal configuration across a front portion of the elastic sleeve in such a fashion as to contact and provide lift and support to the protected joint. Preferably, the support strap is "S" shaped in order to provide additional contact with the joint and to provide lift support to the joint without requiring a second support strap. More preferably, the support brace is reversible so that it might be used on either left or right limb joints.

As it will be realized, the present invention is capable of other different embodiments, and its several details are capable of modifications in various, obvious aspects all without departing from the invention. Accordingly, the drawings and descriptions will be regarded as illustrative in nature and not restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings.

Reference will now be made in detail to the present preferred embodiment of the invention, an example of which is illustrated in the accompanying drawings.

DESCRIPTION OF THE PREFERRED EMBODIMENT

Figures 1, 2:
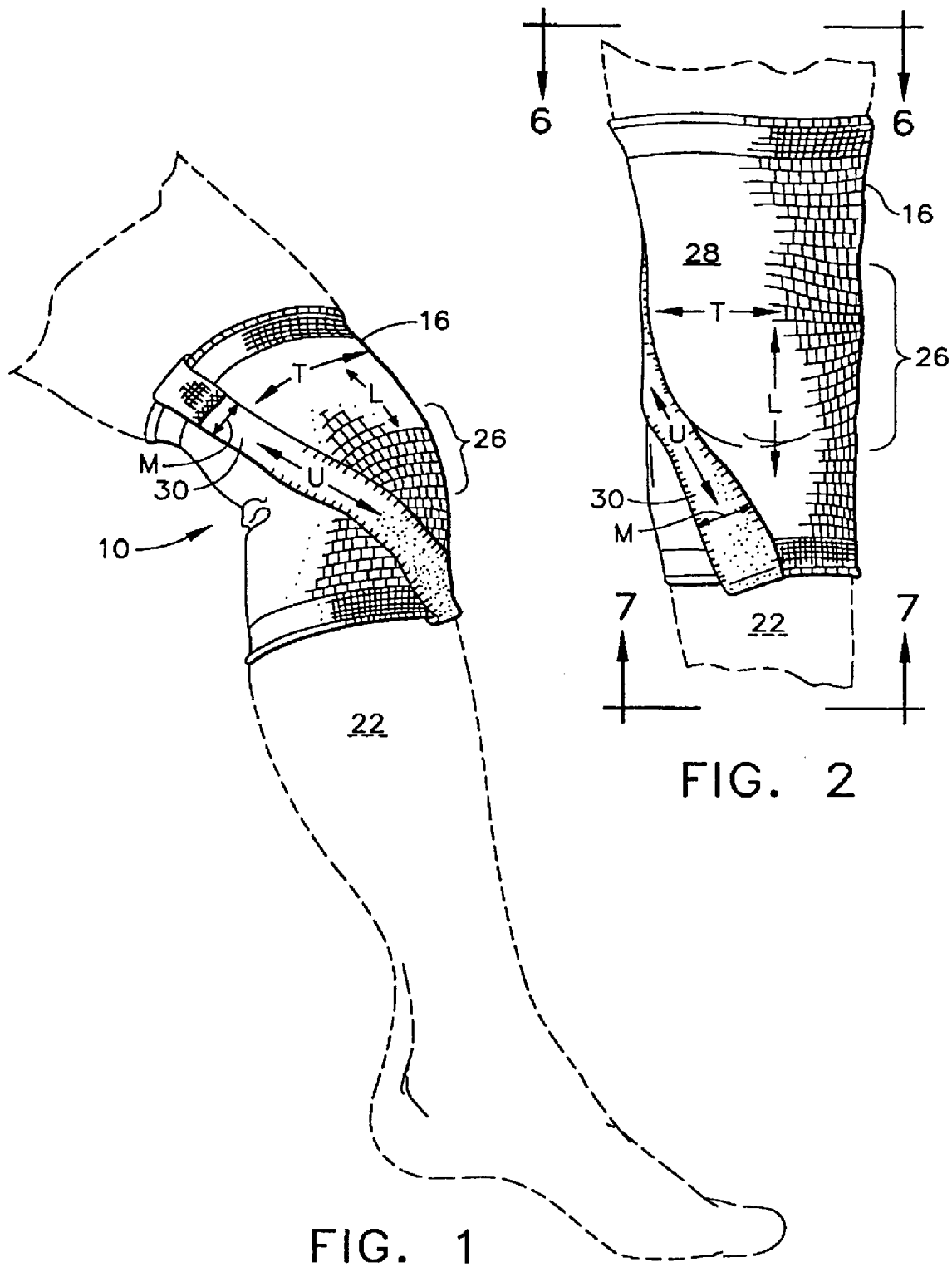
FIG. 1 is a right side elevational view showing the support brace of the present invention about a wearer's right knee.
FIG. 2 is a front elevational view showing the support brace of the present invention about a wearer's right knee.
Figure 3:
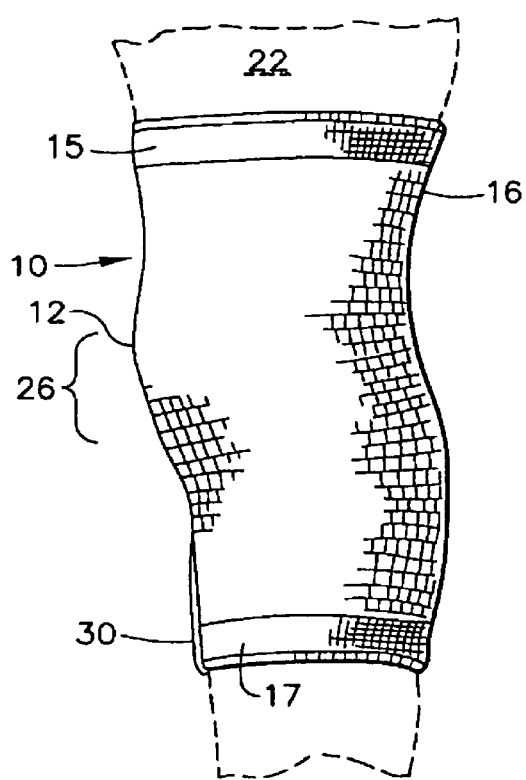
FIG. 3 is a left side elevational view showing the support brace of the present invention about a wearer's right knee.

Reference is now made to FIG. 1 illustrating the support brace 10 of the present invention. As will become apparent by reviewing the description below, the support brace 10 of the present invention provides an effective means for supporting an elbow or knee joint in an efficient and reliable manner.

Figure 6:
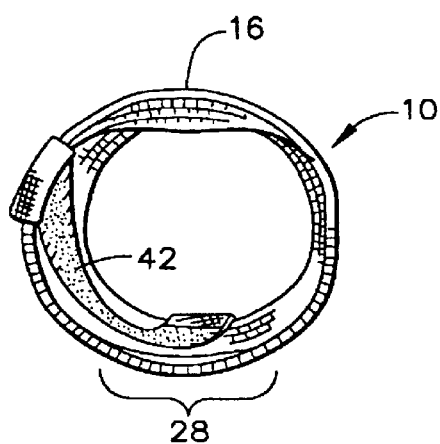
FIG. 6 is a top elevational view showing the support brace of the present invention taken along line 6—6 of FIG. 2.
Figure 7:
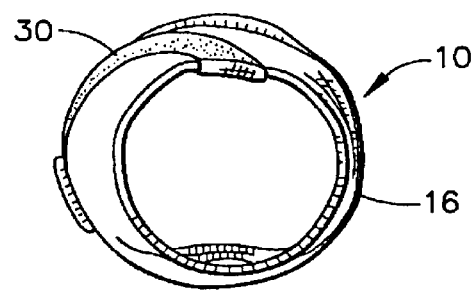
FIG. 7 is a bottom elevational view showing the support brace of the present invention taken along line 7—7 of FIG. 2.
Figure 5:
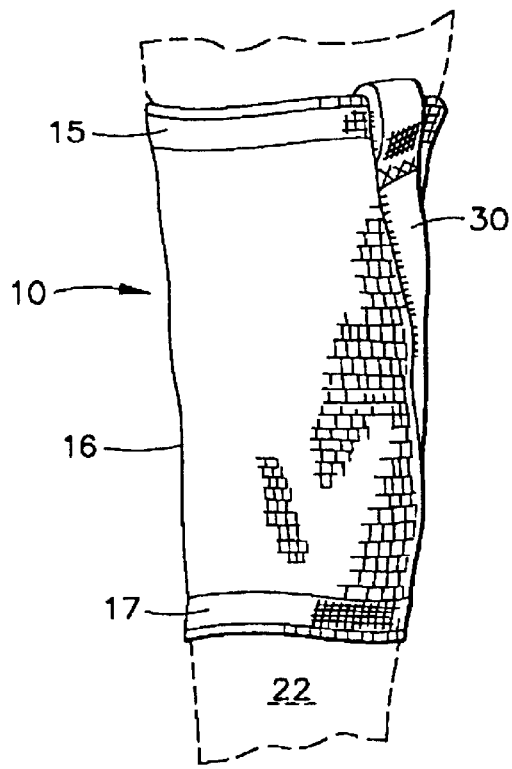
FIG. 5 is a rear elevational view showing the support brace of the present invention about a wearer's right knee.
Figure 8:
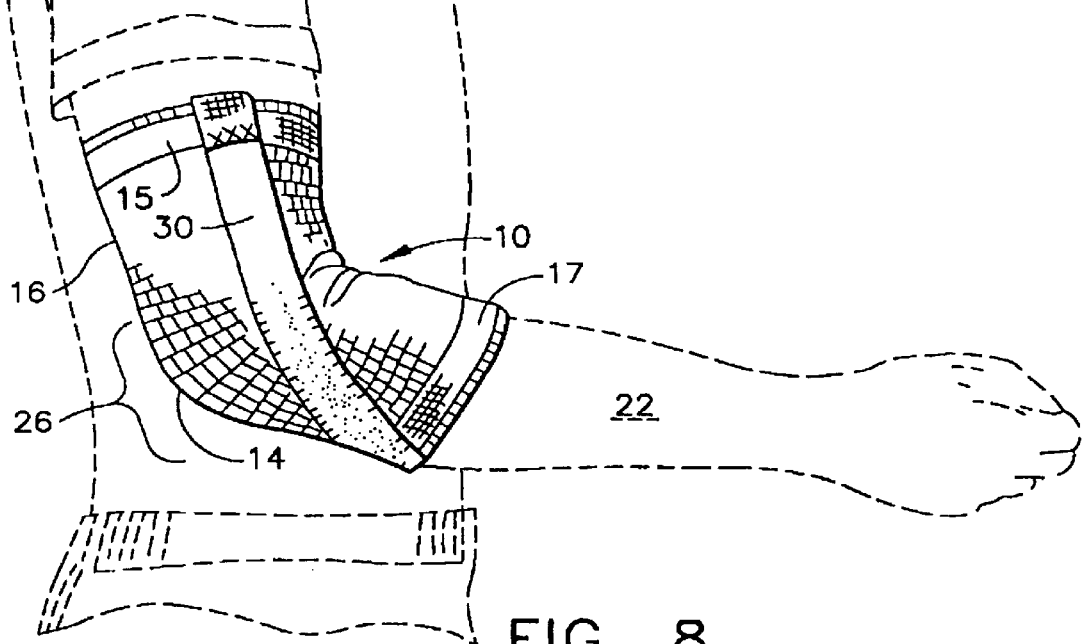
FIG. 8 is right side elevational view showing the support brace of the present invention about a wearer's right elbow.

As best shown in FIGS. 1–8, support brace 10 comprises a sleeve 16 of appropriate size to fit around a knee or elbow joint of a human limb 22 in a stretched configuration. Sleeve 16 comprises an elastic textile material that is elastically stretchable in a transverse direction across the width of support brace 10 (see direction arrows T in FIGS. 1 and 2). Preferably, sleeve 16 comprises woven elastic material to provide greater breathability for the protected joint. Additionally, sleeve 16 is substantially inelastic in a longitudinal direction along the length of support brace 10 (see direction arrows L in FIGS. 1 and 2). This inelasticity in the longitudinal direction helps prevent brace 10 from becoming displaced and riding up or down the wearer's limb during use. Sleeve 16 includes a front portion 28 that comprises a joint site 26. When brace 10 is in use, it should be understood that knee joint 12 or elbow joint 14 is located behind and is adjacent with joint site 26 of sleeve 16. Further, sleeve 16 may optionally include a top rim portion 15 and a bottom rim portion 17. Preferably, top and bottom rim portions 15, 17 comprise elastic material of sufficient elasticity to ensure that brace 10 remains in place during vigorous flexing and exercise of the joint on which brace 10 is worn. Preferably, top and bottom portions 15, 17 are substantially unidirectionally elastic in a transverse direction across the width of support brace 10. The unidirectional elasticity of sleeve 16 advantageously provides beneficial compressive tension across the joint when brace 10 is worn. For example, when the joint on which brace 10 is worn is a knee, the kneecap is pressed inwardly into the leg. Similarly, as shown in FIG. 8, when the brace is worn on an elbow beneficial compressive tension is applied to the elbow joint 14.

In addition, support brace 10 comprises a support strap 30 that is manufactured from an elastic textile material. Strap 30 is elastically stretchable in a longitudinal direction along the length of strap 30 (see direction arrows U in FIGS. 1 and 2). Additionally, strap 30 is substantially inelastic in a transverse direction across its width (see direction arrows M in FIGS. 1 and 2). Strap 30 is attached to the front portion 28 of sleeve 16 in a substantially diagonal configuration across the length of sleeve 16. Further, strap 30 is attached to sleeve 16 in such a manner so that a portion of strap 30 is disposed below and substantially adjacently with joint site 26. The unidirectional elasticity of support strap 30 advantageously provides lift and support to the protected joint when support 10 is worn. Support strap 30 may be attached to sleeve 16 by any suitable manner. Preferably, strap 30 is sewn onto the brace 10. Additionally, sleeve 16 may be cut apart and support strap 30 may be sewn into the resulting gap in order to connect sleeve 16 and form a tubular structure.

In the preferred embodiment, and as best shown in FIGS. 6 and 7, support brace 10 optionally comprises an additional support strap of elastic material 42. This additional strap is fixably attached to an interior surface of the front portion 28 of sleeve 16 in a substantially diagonal configuration. Preferably, support straps 30, 42 are sewn onto sleeve 16 with a zig zag stitch pattern along the length of the straps. As it should be appreciated, this zig zag stitching pattern advantageously allows for straps 30, 42 to readily elastically deform in a longitudinal direction. Similar to strap 30, inner strap 42 includes a portion that is disposed below and substantially adjacent with joint site 26 of sleeve 16. Inner support strap 42 has relatively large elastic qualities in a longitudinal direction along its length, and relatively small elastic qualities in a transverse direction across its width. Although inner strap 42 may have different elastic properties than outer strap 30, it is preferred that support straps 30, 42 have substantially similar elastic qualities. Preferably, inner support strap 42 is substantially aligned with and disposed substantially behind support strap 30. As it should be appreciated, the provision of strap 42 provides additional lift and support to the protected joint. Further, this configuration allows brace 10 to be reversible. Accordingly this reversible feature advantageously allows the brace to be turned inside out and allows it to be used on either a left or right limb joint.

Figure 4:
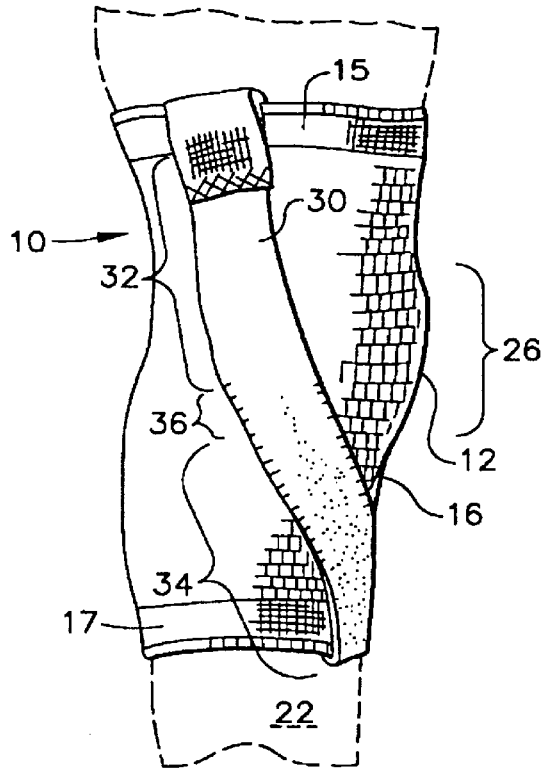
FIG. 4 is a right side elevational view showing the support brace of the present invention about a wearer's right knee.

In the preferred embodiment, support straps 30, 42 are slightly "S" shaped. Specifically, as best shown in FIG. 4, supports straps 30, 42 preferably each include a relatively upwardly concave top portion 32 and a relatively upwardly convex lower portion 34. Upper and lower portions 32, 34 are preferably divided by an inflection point 36. As it should be appreciated, the provision of this "S" shape configuration advantageously provides for more contact between joint site 26 and support strap 16. As a result, significant amounts of lift support is provided to the protected joint. Specifically, the "S" shaped support straps provide improved lift support to the protected joints as compared with the support exhibited by substantially straight diagonal straps. For example, and as best shown in FIG. 4, when the protected joint is a knee, "S" shaped strap 30 comes up and around the kneecap to provide greater lift to the joint.

Preferably, in order to provide additional lift to the protected joint, strap 42, when unstretched, is slightly shorter than strap 30 before straps 30, 42 are fixedly attached to sleeve 16. Strap 42 is preferably slightly stretched when being attached to said sleeve 16 in such a manner so that first and second straps 30, 42 are of substantially equal lengths after being fixedly attached to said sleeve.

In summary, many benefits have been described which result from employing the concepts of the invention. The support brace 10 of the present invention comfortably provides advantageous lift support and compression support to a knee or elbow joint. Additionally, support brace 10 achieves effective and reliable support with a minimal number of requisite parts, thus allowing for the brace to be more economically manufactured.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, support straps 30, 42 may comprise one long strap that includes a portion fixedly attached to the outside of sleeve 16 as well as a portion fixedly attached to an interior surface of sleeve 16 in order to achieve the same reversibility of the support brace as shown and described in the above-described preferred embodiment. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A support brace for knee or elbow comprising:

a sleeve of substantially tubular elastic material, said sleeve having a cross-sectional circumference of such dimensions to fit around a knee or elbow joint of a human limb in a stretched configuration, said sleeve having relatively large elastic qualities in a transverse direction across a width of said limb and relatively small elastic qualities in a longitudinal direction along a length of said limb, said sleeve further having a joint site on a front portion thereof;

a support strap of elastic material, said support strap being fixedly attached to said front portion of said sleeve in a substantially diagonal configuration across a length of said sleeve, a portion of said support strap further being disposed below and substantially adjacently with said joint site, said support strap having relatively large elastic qualities in a longitudinal direction along a length of said support strap and relatively small elastic qualities in a transverse direction across a width of said support strap.

2. The support brace according to claim 1 wherein said support strap is slightly "S" shaped so as to maximize contact of said support strap with joint site.

3. The support brace of claim 2, wherein said support strap includes a relatively upwardly concave top portion and a relatively upwardly convex lower portion, said upper and lower portions further being divided by an inflection point, said inflection point further being located on a portion of said support strap disposed below and substantially adjacently with said joint site.

4. The support brace according to claim 3 wherein said inflection point is located approximately at the midpoint of said support strap.

5. The support brace according to claim 2 wherein said joint is a knee.

6. The support brace according to claim 2 wherein said joint is an elbow.

7. A support brace for knee or elbow comprising:

a sleeve of substantially tubular elastic material, said sleeve having a cross-sectional circumference of such dimensions to fit around a knee and elbow joint of a human limb in a stretched configuration, said sleeve having relatively large elastic qualities in a transverse direction across a width of said limb and relatively small elastic qualities in a longitudinal direction along a length of said limb, said sleeve further having a joint site on a front portion thereof;

a first support strap of elastic material, said first support strap being fixedly attached to an outer surface of said front portion of said sleeve in a substantially diagonal configuration across a length of said sleeve, a portion of said first support strap further being disposed below and substantially adjacently with said joint site, said first support strap having relatively large elastic qualities in a longitudinal direction along a length of said support strap and relatively small elastic qualities in a transverse direction across a width of said support strap;

a second support strap of elastic material, said second support strap being fixedly attached to an interior surface of said front portion of said sleeve in a substantially diagonal configuration across a length of said sleeve, a portion of said second support strap further being disposed below and substantially adjacently with said joint site, said second support strap having relatively large elastic qualities in a longitudinal direction along a length of said support strap and relatively small elastic qualities in a transverse direction across a width of said support strap, said second support strap being substantially aligned with and being disposed substantially behind said first support strap.

8. The support brace according to claim 7 wherein said first and second support straps are slightly "S" shaped so as to maximize contact of said support straps with said joint site.

9. The support brace according to claim 8 wherein said straps each include a relatively upwardly concave top portion and a relatively upwardly convex lower portion, said upper and lower portions further being divided by an inflection point, said inflection point further being located on a portion of a corresponding support strap disposed substantially adjacently with said joint site.

10. The support brace according to claim 9 wherein said inflection points are located approximately at the midpoint of each said support strap.

11. The support brace according to claim 8 wherein said joint is a knee.

12. The support brace according to claim 8 wherein said joint is an elbow.

13. The support brace according to claim 8 wherein said support brace is reversible, said brace being usable on either left or right limb joints.

14. The support brace according to claim 8 wherein said first support strap is relatively longer than said second support strap when said first and second straps are unstretched, wherein said second support strap is slightly stretched while being fixedly attached to said sleeve, and wherein first and second straps are substantially of equal lengths after being fixedly attached to said sleeve.

* * * * *